United States Patent [19]

Wan et al.

[11] Patent Number: 4,523,026
[45] Date of Patent: Jun. 11, 1985

[54] SYNTHESIS OF N-BENZYLOXYCARBONYL-L-ASPARTIC ACID

[75] Inventors: K. Ming Wan, East Brunswick; Mary S. Chen, Edison; Anil D. Pendse, Highland Park, all of N.J.

[73] Assignee: Hatco Chemical Corporation, Fords, N.J.

[21] Appl. No.: 526,581

[22] Filed: Aug. 26, 1983

[51] Int. Cl.³ .......................................... C07C 125/065
[52] U.S. Cl. ..................................................... 560/163
[58] Field of Search ......................................... 560/163

[56] References Cited

U.S. PATENT DOCUMENTS 3,808,190  4/1974  Puhlmans ............................ 560/163
4,293,706  10/1981 Gorman .............................. 560/163
4,345,091  8/1982  Sugiyama ........................... 560/163

OTHER PUBLICATIONS

Roberts, "An Introduction to Modern Experimental Organic Chemistry," pp. 152–158 (1969).
Mortimer, "Chemistry a Conceptual Approach, " pp. 469–473 (1967).
Greenstein, "Chemistry of the Amino Acids," vol. 2, pp. 887–901 (1961).
Dean, "Lange's Handbook of Chemistry, " 12th Ed., pp. 10–60 to 10–62 (1979).

Primary Examiner—Michael L. Shippen
Attorney, Agent, or Firm—Blum, Kaplan, Friedman, Silberman & Beran

[57] ABSTRACT

N-Benzyloxycarbonyl-L-aspartic acid (Z-Asp) is synthesized by adding benzyl chloroformate to a solution of L-aspartic acid and sodium hydroxide at relatively high temperatures of 35°–55° C. and over a wide pH range of 9.2–12.0 and acidifying the sodium salt product. The Z-Asp is prepared in high yields exceeding 90% and purity of better than 99% with only a minor amount of the by-product N-benzyloxycarbonyl aspartyl aspartic acid. The Z-Asp is suitable for conversion to aspartame. Carrying out the reaction at high temperatures significantly reduces cycle time while maintaining a high yield with a low dipeptide and unreacted L-aspartic acid content.

23 Claims, No Drawings

SYNTHESIS OF N-BENZYLOXYCARBONYL-L-ASPARTIC ACID

BACKGROUND OF THE INVENTION

This invention relates to the synthesis of high purity N-benzyloxycarbonyl-L-aspartic acid (Z-Asp) suitable for use in the production of L-aspartyl-L-phenylalanine methyl ester, an artificial sweetener, and more particularly to a method of synthesizing highly pure N-benzyloxycarbonyl-L-aspartic acid at high temperatures.

L-Aspartyl-L-phenylalanine methyl ester, aspartame, is known to be about 160 times sweeter than sucrose in aqueous solution. Thus, the use of aspartame as a low-calorie sweetener makes it a highly desirable end product. Aspartame is generally prepared from Z-Asp. In view of the end use of aspartame in food products as a sugar substitute, the Z-Asp must be as pure as possible and substantially free of by-products generally formed during the formation of the Z-Asp, such as the dipeptide, N-benzyloxycarbonyl aspartyl aspartic acid (Z-Asp-Asp) and sodium chloride.

The reaction of benzyl chloroformate (BCF) with L-aspartic acid (L-AA) to yield Z-Asp has been well known for a number of years. The chemical literature discloses that Z-Asp may be synthesized by the condensation of L-AA with BCF in an alkaline medium. Prior to 1981, the processes described in the literature did not mention the reaction conditions needed to produce Z-Asp with relatively small amounts of by-products.

U.S. Pat. No. 4,293,706 which issued on Oct. 6, 1981 to Gorman, et al. teaches that Z-Asp can be prepared substantially free of Z-Asp-Asp by reacting BCF with the disodium salt of L-AA in an alkaline aqueous system within a specific pH range of between 10.75 and 11.75, and preferably 11.50 to 11.75. The temperature of the reaction is maintained between 10° and 45° C., preferably at room temperature, at which each of the working examples is run. The resulting reaction mixture is acidified to convert the product to the free acid. The patentees caution at column 2, lines 17-25 that when the reaction conditions vary, such as a pH of over 12, significant hydrolysis of the benzyl chloroformate occurs, the Z-Asp product contains more than trace amounts of impurities and the yield is reduced. At column 3, lines 15-22, they also note that as the temperature of the reaction increases, the amount of impurities in the Z-Asp product increases.

U.S. Pat. No. 4,345,091 issued on Aug. 17, 1982 to Sugiyama, et al. claims that high yields of Z-Asp can be obtained by reacting BCF with a sodium or potassium salt of L-AA by carrying out the reaction with the pH maintained within the specific range of 12.0 to 13.5 throughout the reaction. Sugiyama, et al. teach maintaining the temperature of the reaction mixture at 10°-30° C. for 3 hours. The results show increased levels of Z-Asp-Asp when the pH falls below 12.0 together with a decrease in yield. Levels of unreacted L-AA in the Z-Asp crystals are reported to be 0.6 percent and above.

Both the Gorman, et al. and Sugiyama, et al. patentees provide suitable reaction conditions within narrow specific pH ranges for preparing a relatively pure Z-Asp product with relatively small amounts of Z-Asp-Asp by-product. However, it remains desirable to increase further the yield and purity as well as providing other improvements in the synthesis of Z-Asp, such as decreasing the reaction time. Accordingly, it is desirable to provide a method of preparing Z-Asp product at faster rates and containing lesser amounts of unreacted L-aspartic acid than heretofore thought possible.

SUMMARY OF THE INVENTION

Generally speaking, in accordance with the invention, N-benzyloxycarbonyl-L-aspartic acid (Z-Asp) is synthesized by adding benzyl chloroformate (BCF) to an aqueous solution of an alkaline metal salt of L-aspartic acid (L-AA) at relatively high temperatures between about 35° and 55° C. Preferably, the temperature is maintained between about 46° and 50° C. The pH of the reaction mixture may be maintained over a wide range, about 9.2 to 12.0. With the temperature between about 46° and 50° C., the pH is preferably maintained between about 10 and 11. Upon exhaustion of the L-AA, the reaction mixture is acidified to yield the free acid. Alternatively, an organic solvent may be added to the reaction mixture with the BCF, and a buffer system may also be utilized.

These conditions result in high yields equal to or better than 90% with the cycle time of the reaction reduced by a factor of about 2 to 6 times. Purity is equal to or greater than 99% with a reduced amount of unreacted L-AA and only a small amount of the dipeptide by-product, N-benzyloxycarbonyl aspartyl aspartic acid (Z-Asp-Asp) and sodium chloride.

Accordingly, it is an object of the invention to provide an improved process for synthesizing Z-Asp.

It is another object of the invention to provide a method for synthesizing Z-Asp at relatively high temperatures for decreasing the cycle time of the reaction.

It is a further object of the invention to provide an improved process for preparing high purity Z-Asp.

It is a further object of the invention to provide an improved process for preparing high purity Z-Asp containing lesser amounts of unreacted L-AA.

It is another object of the invention to provide a method for preparing Z-Asp suitable for use in producing L-aspartyl-L-phenylalanine methyl ester (aspartame), an artificial sweetener.

It is a further object of the invention to provide an improved process for synthesizing Z-Asp by carrying out the condensation of a dialkali metal salt of L-AA and BCF in the presence of a buffer system.

Still another object of the invention is to provide an improved process for the synthesis of Z-Asp wherein the reaction is carried out at relatively high temperature and over a wide pH range which provides improved yield and purity.

Yet another object of the invention is to provide an improved process for the synthesis of Z-Asp wherein the condensation of BCF and a dialkali metal salt of L-AA may be carried out in the presence of an organic solvent.

Yet a further object of the invention is to provide an improved method of synthesizing Z-Asp wherein the production of by-product Z-Asp-Asp is depressed.

Still another object of the invention is to provide an improved process for the synthesis of Z-Asp by adding BCF mixed with an organic solvent to an aqueous solution of a dialkali metal salt of L-AA at high temperature in the presence of a buffer.

Still other objects and advantages of the invention will in part be obvious and will in part be apparent from the specification.

The invention accordingly comprises the several steps and the relation of one or more of such steps with respect to each of the others, and the product possessing the features and properties which are exemplified in the following detailed disclosure, and the scope of the invention will be indicated in the claims.

DESCRIPTION OF THE PREFERRED EMBODIMENTS

N-Benzyloxycarbonyl-L-aspartic acid (Z-Asp) is the product of the condensation of benzyl chloroformate (BCF) and a dialkali metal salt of L-aspartic acid (L-AA) which is then acidified to convert the Z-Asp dialkali metal salt product to the free acid. The condensation is in accordance with the following equation:

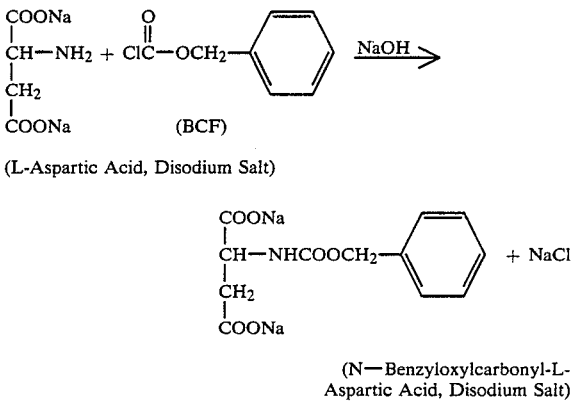

(L-Aspartic Acid, Disodium Salt)

(N—Benzyloxylcarbonyl-L-Aspartic Acid, Disodium Salt)

In accordance with the invention, the synthesis is carried out at high temperatures of about 35° to 55° C. which provides cycle times of about two to three times faster than at room temperature without significant hydrolysis of the BCF. L-Aspartic acid and water are charged into a reaction vessel which has been equipped with a reflux condenser, two dropping funnels, a thermometer, a pH probe and a mechanical stirrer. An aqueous alkali metal hydroxide, such as sodium hydroxide or potassium hydroxide is added under stirring until all the amino acid is dissolved. A substantially stoichiometric quantity of benzyl chloroformate with additional dilute caustic to maintain the reaction mixture at the desired pH between about 9.2 and 12.0, are added simultaneously to the reaction mixture. A slight molar excess of BCF may be added. As noted above, the temperature of the reaction mixture is maintained between about 35° and 55° C., and preferably between 46° and 50° C. The reaction is considered complete when there is little or no unreacted L-AA detected in the system. The reaction mixture is then cooled and extracted with an organic solvent, such as 1,1,1-trichloroethane, chlorobenzene, methylene chloride or toluene. Alternatively, the pH may be adjusted to about 6 to 7 with hydrochloric acid prior to extraction with an organic solvent to remove any less polar by-products or impurities.

The reaction may be carried out in the presence of an organic solvent, such as 1,1,1-trichloroethane, chlorobenzene, 1,1,2-trichloroethane and the like. In this case, the organic solvent is admixed with the benzyl chloroformate prior to the addition of the BCF to the reaction mixture. Addition of an organic solvent to the aqueous phase serves two purposes. First, an organic solvent tends to suppress hydrolysis of the benzyl chloroformate. Second, it aids in the removal of impurities, such as benzyl alcohol, benzyl chloride, dibenzyl carbonate and the like which can be formed during or prior to the reaction. When an organic solvent is used, generally between about 0.02 to 2.00 parts by volume of an organic solvent is mixed with 1 part by volume BCF. After the reaction is completed, the aqueous layer is separated from the organic phase and cooled to about 5°–7° C. gradually. While cooling, concentrated HCl is added slowly with stirring. Crystals of Z-Asp are collected by centrifugation and they are then washed with ice water and dried.

The reaction may also be carried out in the presence of a buffer, such as sodium carbonate, sodium bicarbonate, trisodium phosphate and disodium hydrogen phosphate, which tends to prevent wide flucuations of pH and minimizes localized acidity and side-reactions within the reaction medium. When carrying out the synthesis of Z-Asp in the presence of a buffer, the buffer is added to the reaction mixture after the amino acid is dissolved. For a 73 gram batch of L-AA which represents about 0.55 gram mole, 5 grams of sodium carbonate is used which represents about 7 percent by weight of the amino acid. The amount of buffer may vary between about 4 and 40 percent by weight of the L-AA depending on the nature of the buffer selected.

The initial concentration of L-AA in the reaction vessel expressed as the ratio of grams of $H_2O$/gram of L-AA should be between about 5:1 to 1.5:1. Preferably, the concentration ratio should be about 3:1. Such a concentration combined with the slow addition of benzyl chloroformate and sodium hydroxide to the reaction medium provides satisfactory yields with low levels of unreacted L-AA and low dipeptide production on the order of about 0.2% and less. Highly dilute L-AA is not practical for commercial production due to the decrease in production capacity. Too high a concentration of L-AA in the reaction mixture tends to favor the formation of the dipeptide.

It is generally known that higher reaction temperatures, result in faster rates of reaction. However, benzyl chloroformate is known to be unstable at higher temperatures, thereby favoring the hydrolysis to benzyl alcohol. This is especially true at higher pH's. For this reason it is traditional to store and transport benzyl chloroformate cold, as well as to run reactions involving benzyl chloroformate at room temperatures. At lower temperatures, the reaction rates are slower and excess benzyl chloroformate accumulates in the reaction mixture favoring hydrolysis.

In view of the literature pointing to a low reaction temperature, it is surprising that the reaction in accordance with the invention takes place at high temperature at a rapid rate without significant hydrolysis of the BCF. An unexpected benefit is the wide pH range within which the reaction may be run. The issued patents specify that the pH of the reaction mixture be maintained within narrow pH ranges of one or one-and-one half units, whereas the pH of the reaction mixture in accordance with the invention may be maintained over a range of almost three units.

Z-Asp is synthesized in accordance with the invention as described above while controlling the reaction conditions and reactants. The process is essentially a high temperature process. BCF is reacted with a dialkali metal salt of L-aspartic acid at temperatures between 35° and 55° C. with the pH of the reaction mixture maintained within the broad range, 9.2 to 12.0. Preferably, the temperature of the reaction mixture is maintained between about 46° to 48° C. with the pH of the reaction mixture maintained between about 10.0 and 11.0. In several exemplary embodiments of the invention, the reaction is carried out in the presence of an organic solvent and a buffer. By carrying out the reaction at high temperatures in accordance with the invention, the cycle time of the reaction is reduced substantially by a factor between about 2.5 and 3.0 compared to room temperature and up to 6.0 compared to 10° C.

The following examples of the synthesis of Z-Asp in accordance with the invention are presented by way of illustration only, and are not intended in a limiting sense. The equipment used and the procedure followed were those used in the comparative tests which are set forth following the description of Example 1.

EXAMPLE 1

In a 1 liter multi-necked flask equipped with a reflux condenser, two dropping funnels, a thermometer, a pH probe and mechanical stirrer was placed 39.9 grams (0.300 mole) of L-AA and 120 ml water. A 25% NaOH solution was added with stirring, until the L-AA was fully dissolved. About 55 grams (0.306 mole) of 95% pure BCF was added to the reaction mixture with sufficient dilute NaOH solution with stirring to maintain the reaction medium at a pH range of between 10.75 and 11.75. The temperature was initially 40° C. and it was maintained between about 45° to 48° C. during the addition of the BCF. The pressure of unreacted L-AA in the reaction mixture was monitored by the Ninhydrin method. The reaction was completed after 45 minutes for the start of addition of BCF. At that time little or no unreacted L-AA was detected.

After the reaction was completed, the aqueous system was adjusted to a pH 6–7 with hydrochloric acid and 1,1,1-trichloroethane was added to remove any by-products or impurities. The aqueous layer was separated from the organic phase and cooled to between about 5°–7° C. gradually. While cooling, concentrated HCl was added slowly, with stirring. Crystals were collected by centrifugation, washed with ice water and dried. The dry Z-Asp product weighed 71 grams which represented a yield of about 89%.

EXAMPLE 2

In order to provide a direct comparison to Gorman, et al. (U.S. Pat. No. 4,293,706), the same quantities of reactants and equipment were used as in Example 1, except that the temperature of the reaction medium was maintained between 20°–24° C. These reaction conditions are within the preferred range of Gorman et al. The reactants, reaction conditions and product analysis for these comparative examples are summarized in TABLE I as follows:

TABLE 1

|  | EXAMPLE 1 | EXAMPLE 2 |
|---|---|---|
| REACTANTS |  |  |
| L-AA g. (mole) | 39.90 (0.300) | 39.90 (0.300) |
| BCF % purity, g, (mole) | 95%, 55 (0.306) | 95%, 54 (0.301) |
| Ratio H$_2$O: L-AA | 3:1 | 3:1 |
| Solvent | — | — |
| Na$_2$CO$_3$ (g) | — | — |
| REACTION CONDITIONS |  |  |
| Temp., °C. - Initial | 40 | 20–24 |
| Reaction | 45–48 | 20–24 |
| pH Range | 10.75–11.75 | 10.75–11.75 |
| Reaction Time (Min.) | 45 | 145 |
| PRODUCT ANALYSIS |  |  |
| Yield g, (%) | 71.0 (88.6) | 70.0 (87.5) |
| Assay %* | 100.30 | 99.60 |
| Dipeptides %** | 0.11 | 0.08 |
| L-AA % | 0.20 | 0.40 |
| NaCl %* | 0.40 | 0.40 |
| Thin Layer Chromatography (TLC) | one spot | one spot |

*Analyzed by titration
**Analyzed by high pressure liquid chromatography (HPLC)

As can be seen in Example 2 which was run at or about room temperature the reaction took 145 minutes to complete, whereas the high temperature synthesis in accordance with the invention was completed within 45 minutes without sacrificing yield or purity. The concentration of unreacted L-AA in the Z-Asp product of Example 1 is also one-half that of Example 2. Thin layer chromatography also indicated that the products were substantially free from polar or non-polar impurities. These results show that the purity of the products of the high temperature reactions were at least equal to that of the low temperature process.

EXAMPLES 3 AND 4

The following two Examples illustrate the condensation of L-AA and BCF in the presence of an organic solvent. In Example 3 chlorobenzene was mixed with the BCF and in Example 4 the solvent 1,1,1-trichloroethane was used. The procedure of Example 1 was followed. The following reactants and reaction conditions are set forth in TABLE II as are the results which were obtained:

TABLE II

|  | EXAMPLE 3 | EXAMPLE 4 |
|---|---|---|
| REACTANTS |  |  |
| L-AA g. (mole) | 39.9 (0.300) | 39.9 (0.300) |
| BCF % purity, g, (mole) | 97%, 54.5 (0.310) | 97%, 56.0 (0.318) |
| Ratio H$_2$O: L-AA | 3:1 | 3:1 |
| Solvent | 48 ml chlorobenzene | 20 ml TCE |
| REACTION CONDITIONS |  |  |
| Temp., °C. - Initial | 40 | 35 |
| Reaction | 48–50 | 35–40 |
| pH Range | 11.00–11.50 | 11.75–12.00 |
| Reaction Time (Min.) | 40 | 100 |
| PRODUCT ANALYSIS |  |  |
| Yield g, (%) | 73.6 (91.9%) | 70.5 (87.9%) |
| Assay % | 99.58 | 99.67 |
| Dipeptides % | 0.06 | 0.05 |
| L-AA % | 0.1 | 0.2 |
| NaCl % | trace | 0.2 |

EXAMPLES 5–8

In Examples 5–8 reported in TABLE III, the condensation of benzyl chloroformate and the sodium salt of L-AA was carried out in the presence of a buffer. In Examples 5 and 6 a sodium carbonate buffer was present and in Example 7, trisodium phosphate was present. In Example 8 the benzyl chloroformate was mixed with 1,1,1-trichloroethane prior to addition to the reaction mixture which included a sodium carbonate buffer. In each case, the procedure of Example 1 was followed.

TABLE III

|  | EXAMPLE 5 | EXAMPLE 6 | EXAMPLE 7 | EXAMPLE 8 |
| --- | --- | --- | --- | --- |
| REACTANTS |  |  |  |  |
| L-AA g. (mole) | 26.6 (0.200) | 39.9 (0.300) | 39.9 (0.300) | 39.9 (0.300) |
| BCF % purity, g, (mole) | 95% 36 (0.200) | 95% 55 (0.306) | 95% 54 (0.301) | 95% 55 (0.306) |
| Ratio $H_2O$: L-AA | 3:1 | 3:1 | 3:1 | 3:1 |
| Solvent | — | — | — | TCE 20 ml |
| $Na_2CO_3$ (g) | 4 | 3 | — | 3 |
| $Na_3PO_4.12H_2O$ (g) | — | — | 8 | — |
| REACTION CONDITIONS |  |  |  |  |
| Temp., °C. - Initial | 40 | 40 | 40 | 35 |
| - Reaction | 45–50 | 47–50 | 46–48 | 45–48 |
| pH Range | 9.40–9.60 | 10.10–10.75 | 10.50–11.10 | 10.20–10.75 |
| Reaction Time (Min.) | 30 | 30 | 25 | 60 |
| PRODUCT ANALYSIS |  |  |  |  |
| Yield g, (%) | 47.5 (88.9%) | 73.8 (92.0%) | 76.5 (95.5%) | 75.8 (94.3%) |
| *Assay % | 100.10 | 99.90 | 99.80 | 99.13 |
| **Dipeptides % | 0.17 | 0.11 | 0.10 | 0.10 |
| L-AA % | $\leq 0.20$ | $\leq 0.20$ | trace | $\leq 0.20$ |
| *NaCl % | $\leq 0.30$ | 0.30 | 0.20 | $\leq 0.30$ |

*Analyzed by titration
**Analyzed by HPLC in area %

Based on the results in TABLES I, II and III, it is apparent the Z-Asp can be obtained in yields approaching and exceeding 90% with low dipeptide content at high temperatures, such as between 45° C. and 50° C. over a wide pH range. At these high temperatures the reaction rate is about 3.0 times faster than at room temperature while maintaining product quality. Most significantly, the concentration of unreacted L-AA in the Z-Asp product is consistently one-half or less than obtained by using prior art processes.

The organic solvent minimizes the hydrolysis of benzyl chloroformate, tends to remove organic impurities in the system and also improves the quality of the end product. It is noted that some solvents perform better than others in this system. Addition of a buffer tends to improve results at the lower pH range, as shown by the results of Example 5. The presence of a buffer prevents wide flucuations of the pH range and minimizes dipeptide formation and hydrolysis of benzyl chloroformate as demonstrated by the examples.

In accordance with the invention, Z-Asp at higher yields and higher purity than heretofore thought possible is obtained by carrying out the condensation of L-AA and benzyl chloroformate at high temperatures over a wide pH range. Carrying out the synthesis at high temperatures substantially reduces the reaction time and provides Z-Asp in yields and purity heretofore not possible.

It will thus be seen that the objects set forth above, among those made apparent from the preceding description, are efficiently attained and, since certain changes may be made in carrying out the above process and in the described product, set forth without departing from the spirit and scope of the invention, it is intended that all matter contained in the above description shall be interpreted an illustrative and not in a limiting sense.

It is also to be understood that the following claims are intended to cover all of the generic and specific features of the invention herein described, and all statements of the scope of the invention which, as a matter of language, might be said to fall therebetween.

Particularly, it is to be understood that in said claims, ingredients or compounds recited in the singular are intended to include compatible mixtures of such ingredients wherever the sense permits.

What is claimed is:

1. A method of synthesizing N-benzyloxycarbonyl-L-aspartic acid by condensing benzyl chloroformate and a dialkali metal salt of L-aspartic acid in aqueous solution, comprising adding benzyl chloroformate and an alkali metal hydroxide solution to an alkaline aqueous mixture containing L-aspartic acid while maintaining the temperature of the reaction mixture above 45° C. and at a pH of at least 9.2 and upon completion of the reaction acidifying the reaction mixture.

2. The method of claim 1, wherein the temperature of the reaction mixture is maintained above 45° to about 55° C.

3. The method of claim 1, wherein the temperature of the reaction mixture is maintained between about 46° and 50° C.

4. The method of claim 1, wherein the pH of the reaction mixture is maintained between about 9.2 and 12.

5. The method of claim 3, wherein the pH of the reaction mixture is maintained between about 10.0 and 11.0.

6. The method of claim 1, further including the step of mixing the benzyl chloroformate with an organic solvent prior to adding the benzyl chloroformate to the reaction mixture containing L-aspartic acid.

7. The method of claim 6, wherein the solvent is present in amounts between about 0.2 to 2 parts by volume of organic solvent to 1 part by volume of benzyl chloroformate.

8. The method of claim 6, wherein the organic solvent is selected from the group consisting of 1,1,1-trichloroethane, chlorobenzene and 1,1,2-trichloroethane.

9. The method of claim 1, wherein the L-aspartic acid is present in the reaction mixture in a concentration between about 15% to 60% by weight.

10. The method of claim 1, further including the step of monitoring the presence of L-aspartic acid in the reaction mixture and adding the benzyl chloroformate to the reaction mixture until only a trace amount of L-aspartic acid is present therein.

11. The method of claim 1, wherein the alkali metal hydroxide is sodium hydroxide.

12. The method of claim 11, wherein the temperature of the reaction mixture is maintained between about 46° C. and 50° C.

13. The method of claim 12, wherein the pH of the reaction mixture is maintained between about 10.0 to 11.0.

14. The method of claim 13, further including the step of mixing the benzyl chloroformate with an organic solvent prior to adding the benzyl chloroformate to the reaction mixture including L-aspartic acid and sodium hydroxide.

15. The method of claim 1, wherein the reaction mixture is acidified with HCl.

16. The method of claim 15, further including the steps of mixing the acidified reaction mixture with an organic solvent, allowing the mixture to separate into an aqueous and an organic phase and separating the aqueous phase prior to acidifying.

17. A method of synthesizing N-benzyloxycarbonyl-L-aspartic acid, comprising:

forming an alkaline aqueous reaction mixture of L-aspartic acid and sufficient sodium hydroxide to dissolve the L-aspartic acid;

gradually adding benzyl chloroformate to the reaction mixture;

maintaining the pH of the reaction mixture between about 9.2 and 12.0 by adding sodium hydroxide to the reaction mixture;

maintaining the temperature of the reaction mixture from at least above 45° C. to about 55° C.;

continuing to add the benzyl chloroformate and sodium hydroxide to the reaction mixture and monitoring the presence of unreacted L-aspartic acid in the reaction mixture until only a trace amount of the L-aspartic acid remains; and acidifying the reaction mixture.

18. The method of claim 17, including the step of maintaining the pH of the reaction mixture between about 10.0 and 11.0 and the temperature between about 46° and 50° C.

19. The method of claim 17, including the step of introducing an organic solvent to the reaction mixture with the benzyl chloroformate.

20. The method of claim 17, further including the steps of mixing the acidified reaction mixture with an organic solvent, allowing the mixture to separate into an aqueous and an organic phase, and separating the aqueous phase prior to acidifying the reaction mixture.

21. A method of synthesizing an alkali metal salt of N-benzyloxycarbonyl-L-aspartic acid comprising adding benzyl chloroformate and an alkali metal hydroxide solution to an alkaline aqueous reaction mixture of L-aspartic acid and an alkali metal hydroxide while maintaining the temperature of the reaction mixture from at least above 45° C. to about 55° C.

22. The method of claim 21, wherein the alkali metal hydroxide is sodium hydroxide and the dialkali metal salt of N-benzyloxycarbonyl-L-aspartic acid is the disodium salt.

23. The method of claim 21, wherein the temperature of the reaction mixture is maintained between about 46° C. and 50° C.

* * * * *